United States Patent [19]
Wong et al.

[11] Patent Number: 5,973,174
[45] Date of Patent: Oct. 26, 1999

[54] PREPARATION OF TRANSITION METAL CATALYSTS FROM PHOSPHONIUM SALTS

[75] Inventors: Pui Kwan Wong; Manuel Soler Rodriguez, both of Houston; Andrew Allison Moxey, Richardson, all of Tex.

[73] Assignee: Shell Oil Company, Houston, Tex.

[21] Appl. No.: 09/198,813

[22] Filed: Nov. 24, 1998

[51] Int. Cl.$^6$ ............................ C07F 15/00; C07C 45/00
[52] U.S. Cl. ................ 556/18; 556/136; 568/9; 568/10; 568/451; 568/454
[58] Field of Search ................ 568/9, 10, 451, 568/454; 556/18, 136

[56] References Cited

U.S. PATENT DOCUMENTS

| | | | |
|---|---|---|---|
| 4,122,123 | 10/1978 | Hestermann et al. | 260/606.5 F |
| 4,691,047 | 9/1987 | Drent | 560/204 |
| 4,861,912 | 8/1989 | Drent et al. | 560/204 |
| 4,892,687 | 1/1990 | Lin | 260/404 |
| 5,028,734 | 7/1991 | Drent | 560/207 |
| 5,256,827 | 10/1993 | Slaugh et al. | 568/454 |
| 5,304,674 | 4/1994 | Drent | 560/204 |
| 5,304,686 | 4/1994 | Slaugh et al. | 568/486 |
| 5,780,684 | 7/1998 | Drent et al. | 568/454 |

FOREIGN PATENT DOCUMENTS

| | | |
|---|---|---|
| 1 341 857 | 12/1973 | European Pat. Off. . |
| 121965 | 10/1984 | European Pat. Off. . |
| 2 101 601 | 1/1983 | United Kingdom . |
| 2323359 | 9/1998 | United Kingdom . |

*Primary Examiner*—Porfirio Nazario-Gonzalez
*Attorney, Agent, or Firm*—Del S. Christensen

[57] ABSTRACT

A method is provided to prepare a cationic transition metal catalyst, the method including the steps of: providing a disubstituted phosphine selected from the group consisting of RPH and $R_1R_2PH$ wherein R is a divalent group selected from substituted and nonsubstituted hydrocarbon groups, $R_1$ and $R_2$ are independently selected from substituted and nonsubstituted hydrocarbon groups; combining the disubstituted phosphine with a salt of the formula $R_3X_n$ wherein X is a good leaving group and is a weakly coordinating anion and $R_3$ is a substituted or nonsubstituted aliphatic hydrocarbon and n is 1, 2, or 3 to form a phosphonium salt of a formula selected from $R_3(RP^+H)_nnX^-$ and $R_3(R_1R_2P^+H)_nnX^-$; and combining the phosphonium salt with a transition metal salt of the formula $MY_m$ wherein M is a transition metal, and Y is the anion of a weak acid thereby forming a cationic transition metal catalyst.

10 Claims, No Drawings

PREPARATION OF TRANSITION METAL CATALYSTS FROM PHOSPHONIUM SALTS

FIELD OF THE INVENTION

The invention relates to a method to prepare homogenous catalysts by combining transition metal salts and a tertiary phosphonium salt containing a weakly coordinating anion.

BACKGROUND TO THE INVENTION

Numerous useful processes are catalyzed by transition metal cationic complexes derived from a combination of a transition metal salt, a phosphine ligand, and a strong acid having a weakly or non-coordinating anion. Examples of such processes include hydroformylation of internal olefins, hydroformylation of α-olefins, acrylic acid produced from acetylene, copolymerization of olefins and carbon monoxide, and production of methyl propionate from ethylene. These cationic phosphine catalysts are typically stable in air, but phosphine precursors to these catalysts can be sensitive to exposure to air. Further, these catalysts have been prepared by multistep synthesis.

For example, U.S. Pat. No. 4,691,047 discloses a process for carbonylation of conjugated dienes with carbon monoxide and an alcohol or water in the presence of an aprotic solvent and a catalytic system prepared by combining a divalent palladium compound, a triarylphosphine and hydrochloric acid. U.S. Pat. No. 5,304,674 discloses an improvement to this process by adding a second diphosphine ligand having electron-releasing substituents on the phosphorus atoms.

European patent application 121,965 A2, 1984, discloses a process for copolymerization of ethylene with carbon monoxide in the presence of methanol using a catalytic system prepared by combining palladium acetate, a diphosphine and p-toluenesulfonic acid.

U. K. patent application 2,101,601A suggests a method to produce bisphosphines by preparation of the bisphosphonium salt followed by hydrolysis of the salt to yield the bisphosphine oxide and then reduction of the bisphosphine oxide to yield a bisphoshine. This method requires an additional process step; a relatively expensive reduction step.

It is therefore an object of the present invention to provide a process to produce a phosphonium salt that can be useful as a component of a catalyst system for reactions between carbon monoxides and olefinic hydrocarbons wherein reactants are not sensitive to exposure to oxygen, and wherein the number of process steps in the process is reduced.

SUMMARY OF THE INVENTION

These and other objects are accomplished by a method to prepare a cationic transition metal catalyst, the method comprising the steps of:

providing a disubstituted phosphine selected from the group consisting of RPH and $R_1R_2PH$ wherein R is a divalent group selected from substituted and nonsubstituted hydrocarbon groups, $R_1$ and $R_2$ are independently selected from substituted and nonsubstituted hydrocarbon groups;

combining the disubstituted phosphine with a salt of the formula $R_3X_n$ wherein X is a good leaving group and is a weakly coordinating anion and $R_3$ is a substituted or nonsubstituted aliphatic hydrocarbon and n is 1, 2, or 3 to form a phosphonium salt of a formula selected from $R_3(RP^+H)_nnX^-$ and $R_3(R_1R_2P^+H)_nnX^-$; and combining the phosphonium salt with a transition metal salt of the formula $MY_m$ wherein M is a transition metal, and Y is the anion of a weak acid thereby forming a cationic transition metal catalyst.

Preferred transition metals include palladium and platinum, and preferred anions of weak acids include acetate and acetoacetonate. These phosphonium transition metal salt catalysts can be useful as catalysts for various reactions involving addition of carbon monoxide to olefinic hydrocarbons.

DESCRIPTION OF A PREFERRED EMBODIMENT

Useful disubstituted phosphines in the present invention are of the formula:

wherein $R_1$ and $R_2$ are independently selected hydrocarbon groups which may be substituted or nonsubstituted. The hydrocarbon groups may contain, for example, aromatic rings, substituted aromatic rings, or saturated rings. Useful groups include, for example, substituted or nonsubstituted groups such as phenyl, naphthyl, o-methoxypnenyl, p-tolyl, o-tolyl, m-chlorophenyl and p-chlorophenyl, or substituted or nonsubstituted aliphatic groups and may be monovalent or divalent. Useful aliphatic groups include optionally branched or cyclic alkyl or alkylene groups having from 1 to 20 carbon atoms, such as methyl, ethyl, propyl, isopropyl, n-butyl, s-butyl, t-butyl, cyclohexyl, pentamethylene, hexamethylene and cyclooctylene.

The salt of the present invention of the formula:

may be selected from a wide variety of salts. X is a good leaving group and is a weakly coordinating anion. An anion from an acid having a $pK_a$ of two or less is considered to be, for the purpose of the present invention, good leaving group. A weakly coordinating anion is defined, for the purpose of the present invention, to be one which results in little or no covalent interaction between a transition metal ion and the anion. Examples of such weakly coordinating anions include, for example, $CF_3CO_2^-$, $CF_3SO_3^-$ and $CH_3C_6H_5SO_3^-$.

"n" may be 1, 2, or 3, and is preferably 2. The value of n of 1, 2, or 3 determines whether the resultant phosphonium salt if a monodentate, bidentate, or tridentate, respectively.

$R_3$ is an aliphatic hydrocarbon group. $R_3$ may be substituted or nonsubstituted. $R_3$ may be part of a cyclic structure, e.g., an aromatic or cycloaliphatic group. $R_3$ may also be an optionally substituted alkylene group having at least two carbon atoms in the chain, but is preferably a two to six carbon atom containing aliphatic group. Suitable $R_3$ groups are the taught in U.S. Pat. Nos. 4,691,047, 4,861,912, 5,028,734, and 5,304,674, incorporated herein by reference, as the bridging groups in the polydentate lingands disclosed in those references.

The salt and disubstituted phosphine of the present invention may be combined in a suitable solvent such as acetonitrile. These components may be combined at atmospheric pressure under sufficient heat to provide a reasonable rate of reaction, or optionally, combined at a lower temperature, and heated to a temperature which results in a reasonable rate of reaction. Heating a solution of the components dissolved in acetonitrile at the boiling point temperature of the mixture is preferred.

EXAMPLE 1,2-bis(9-phosphabicyclo[3.3.1 ]non-9-yl)ethane, (BICYCLO-2), was prepared by a method of the prior art by combining 9-phosphabicylclo[3.3.1]nonane (7.27 grams) and ethylene glycol ditosylate (7.89 grams) in 50 ml of acetonitrile and heating at reflux under an atmosphere pressure of nitrogen for 24 hours. The solution of reactants was then cooled to room temperature, and a precipitate was collected by filtration and washed with acetonitrile, toluene, and acetonitrile, respectively, to yield 7.5 grams of the tosylate salt of 1,2-bis(9-phosphabicyclonon-9-yl)ethane, (BICYCLO-2Ts). The structure of the tosylate salt was confirmed by adding two moles of p-toluene sulfonic acid to one mole of 1,2-bis(9-phosphabicyclononyl)ethane in acetonitrile. The two batches of tosylate salt were identical in $^{13}C$ $^{1}H$ and $^{31}P$ NMR spectra.

Comparative hydroformylation experiments were carried out at 105° C. under 800 psig of 2/1 $H_2CO$ mixture for 24 hours using the following two recipes:

| COMPONENT | PRIOR ART | INVENTION |
|---|---|---|
| Pd(OAc)$_2$ | 1 mmol | 1 mmol |
| BICYCLO-2 | 1.15 mmol | |
| TsOH | 2.3 mmol | |
| BICYCLO-2Ts | | 1.15 mmol |
| NaI | 0.5 mmol | 0.5 mmol |
| 1-OCTENE | 50 ml | 50 ml |
| SULFOLANE | 10 ml | 10 ml |
| 2-ETHYLHEXANOL | 40 ml | 40 ml |
| WATER | 0.5 ml | 0.5 ml |

1-Octene was 100% reacted in both experiments, and the percent of resultant nonanol that was linear was 76.21 % in the prior art experiment and 77.33% with the catalyst produced by the process of the present invention. Conversion to saturated products was 2.0% in the prior art experiment and 1.4% with the present invention.

This experiment demonstrates that the present invention can produce carbonylation catalysts that are indistinguishable from prior art carbonylation catalysts, with the advantages of starting with uses an air-sensitive intermediate and with a simpler process to produce the catalyst.

We claim:

1. A method to prepare a cationic transition metal catalyst, the method comprising the steps of:

providing a disubstituted phosphine selected from the group consisting of RPH and $R_1R_2PH$ wherein R is a divalent group selected from substituted and nonsubstituted hydrocarbon groups, $R_1$ and $R_2$ are independently selected from substituted and nonsubstituted hydrocarbon groups;

combining the disubstituted phosphine with a salt of the formula $R_3X_n$ wherein X is a good leaving group and is a weakly coordinating anion and $R_3$ is a substituted or nonsubstituted aliphatic hydrocarbon and n is 1, 2, or 3 to form a phosphonium salt of a formula selected from $R_3(RP^+H)_n nX^-$ and $R_3(R_1R_2P^+H)_n nX^-$; and combining the phosphonium salt with a transition metal salt of the formula $MY_m$ wherein M is a transition metal, and Y is the anion of a weak acid thereby forming a cationic transition metal catalyst.

2. The method of claim 1 wherein Y is selected from the group consisting of acetate and acetoacetonate.

3. The method of claim 1 wherein M is selected from the group consisting of palladium and platinum.

4. The method of claim 1 further comprising the step of using the homogenous catalyst in a process involving reaction of carbon monoxide with an olefinic hydrocarbon.

5. The method of claim 4 further comprising the step of using the homogenous catalyst in a hydroformylation process.

6. The method of claim 4 further comprising the step of using the homogenous catalyst to copolymerize carbon monoxide and an olefin.

7. The method of claim 1 wherein $R_1$ and $R_2$ are independently selected from the group consisting of: phenyl, naphthyl, o-methoxypnenyl, p-tolyl, o-tolyl, m-chlorophenyl, p-chlorophenyl, methyl, ethyl, propyl, isopropyl, n-butyl, s-butyl, t-butyl, cyclohexyl, pentamethylene, hexamethylene, and cyclooctylene.

8. The method of claim 1 wherein at least one of groups $R_1$, $R_2$, and R is a substituted group.

9. The method of claim 8 wherein the substituted group is substituted with an oxygen containing group.

10. The method of claim 1 wherein X is selected from the group consisting of $CF_3CO_2^-$, $CF_3SO_3^-$ and $CH_3C_6H_4SO_3^-$.

* * * * *